United States Patent [19]
Strickler et al.

[11] Patent Number: 6,137,015
[45] Date of Patent: Oct. 24, 2000

[54] PROCESS AND EQUIPMENT FOR THE PRODUCTION OF ETHYLENE GLYCOLS

[75] Inventors: Gary R. Strickler; Von G. Landon; Guo-shuh John Lee, all of Midland; William J. Rievert, Beaverton, all of Mich.

[73] Assignee: The Dow Chemical Company, Midland, Mich.

[21] Appl. No.: 09/206,888

[22] Filed: Dec. 8, 1998

Related U.S. Application Data

[60] Provisional application No. 60/069,972, Dec. 18, 1997.
[51] Int. Cl.7 .................................................. C07C 27/00
[52] U.S. Cl. .............................................. 568/867
[58] Field of Search ............................. 568/867

[56] References Cited

U.S. PATENT DOCUMENTS 5,763,691   6/1998   Kawabe et al. .

*Primary Examiner*—Paul J. Killos
*Attorney, Agent, or Firm*—Elisabeth T. Jozwiak; John B. Treangen

[57] ABSTRACT

A process for preparing alkylene glycols including reacting an alkylene oxide with water in the presence of a combination of additives and an anion exchange resin, wherein the combination of additives comprises carbon dioxide and an organic or inorganic base provided in an amount sufficient to maintain a pH of the reaction mixture between about 5.0 and 9.0, with the proviso that, when the base is bicarbonate or carbonate, then the anion exchange resin is a trimethyl benzyl ammonium anion exchange resin. A particularly preferred method of this invention is to react ethylene oxide with water in the presence of a halogenate or bicarbonate-type anionic exchange resin (such as a DOWEX™ MSA-1 type resin), carbon dioxide, and sodium hydroxide. Some advantages of this invention are that it provides desirable catalyst lifetime and activity, minimizes resin swelling, and provides a desirable, sustained selectivity to alkylene glycol.

20 Claims, No Drawings

PROCESS AND EQUIPMENT FOR THE PRODUCTION OF ETHYLENE GLYCOLS

This application claims the benefit of U.S. Provisional Application No. 60/069,972, filed Dec. 18, 1997 (incorporated herein by reference).

BACKGROUND OF THE INVENTION

This invention relates to a catalytic process for preparing alkylene glycols, preferably ethylene glycol, from alkylene oxide and water.

Alkylene glycols, such as ethylene glycol and propylene glycol, are widely used as raw materials in the production of polyesters, polyethers, antifreeze, solution surfactants, and as solvents and base materials in the production of polyethylene terephthalates (e.g. for fibers or bottles). Commercial processes for the preparation of alkylene glycols typically involve the liquid phase hydration of the corresponding epoxide in the presence of a large molar excess of water (see, e.g., Kirk-Othmer, *Encyclopedia of Chemical Technology*, Vol. 11, Third Edition, page 929 (1980)). The primary by-products of the hydrolysis reaction are di-, tri-, and higher glycols. However, as compared to monoalkylene glycols, the demand for di-, tri-, tetra-, and polyalkylene glycols is low. The formation of the di- and polyglycols is believed to be primarily due to the reaction of the epoxide with alkylene glycols. As epoxides are generally more reactive with glycols than they are with water, a large excess of water is employed in order to favor the reaction with water and thereby obtain a commercially attractive selectivity to the monoglycol product. However, even in light of the large excess of water, a typical commercially practiced method for making ethylene glycol has a molar selectivity to monoethylene glycol (MEG) of between 80 to about 90 percent (%), a molar selectivity to diethylene glycol (DEG) of between 9 to about 15%, and a molar selectivity to triethylene glycol (TEG) of between 1 to 5%. In addition, increasing the water to epoxide feed ratio also increases the cost of distilling water from the glycol. Thus, there is much interest in alternative processes that increase monoalkylene glycol selectivity without increasing production costs.

One such alternative is a heterogeneous catalytic process such as the use of a selectivity-enhancing metalate anion-containing material. See, for example, EP-A-156,449. Typical metalate anions consist of anions of molybdate, tungstate, metavanadate, hydrogenpyrovanadate and pyrovanadate. Such a process can demonstrate acceptable conversions, good selectivity, and a low water/alkylene oxide ratio. Moreover, U.S. Pat. Nos. 4,277,632 and 4,982,021 disclose the use of a pH adjusting additive to enhance the performance of the metalate-containing materials. However, a disadvantage of such processes is that the alkylene glycol-containing product stream also comprises a substantial amount of metalate anions which have been displaced from the electropositive complexing sites of the solid metalate anion-containing material. Therefore, an additional separation step is required in order to remove the metalate anions from the product.

One variation of a heterogeneous catalytic process is based on catalytic hydration of ethylene oxides in the presence of carbon dioxide and an anion-exchange resin in the halogen form. See, for example, JP-A-57-139026. Such halogen type anion exchange resins include halides of chlorine, bromine, and iodine, and in particular, basic anion exchange resins. Disclosed as being especially suitable is a chloride form anion exchange resin such as DOWEX™ MSA-1, which is an anon-exchange resin containing benzyl trimethyl ammonium groups as electropositive centers. A disadvantage of this process is that the product stream contains a mixture of both glycols and carbonates. Isolation of the glycols from the mixture is difficult because the boiling temperatures of di-glycols and carbonates are close to each other. In addition, separation of ethylene glycol is further complicated due to the close relative volatility of ethylene glycol and ethylene carbonate at low concentrations of ethylene carbonate in ethylene glycol.

Yet another variation utilizes a similar process of reacting alkylene oxide and water in the presence of carbon dioxide, but utilizes a bicarbonate form of the anion exchange resin. See, for example, Russian Patent Nos. 2002726 and 2001901. In the cited Russian publications it is specifically disclosed to use Anionites AV-17 and AV-17-T as the anion exchange resins. These are disclosed as polystyrenes cross-linked with divinylbenzene and having quaternary ammonium groups in the bicarbonate form. The Russian publications further disclose use of carbon dioxide in amounts ranging from at least as low as 0.01 weight percent (wt %). This variation of the process attempts to eliminate the difficult separation of the alkylene glycol product from the carbonate, but it still suffers from the disadvantage of having an undesirably low productivity or activity at temperatures that do not cause rapid loss of catalyst activity (<130° C.). The activity can be improved by operating at higher temperatures, but the catalyst rapidly loses activity at high temperature, thus the catalyst must be replaced often. Large amounts of catalyst are required in either case. Furthermore, the selectivity is relatively low compared to systems that operate without carbon dioxide.

In WO/20559A, it is pointed out that the aforementioned Russian publications (similar to the halogenate-type resin publications) do not dispense with the addition of carbon dioxide to the feed. According to WO/20559A, carbon dioxide is detrimental to the catalytic effect of bicarbonate-exchanged resins of the quaternary ammonium type and it is disclosed to perform the process in the substantial absence of carbon dioxide. However, the process described in WO/20559A suffers from the disadvantage of having an undesirably short catalyst lifetime and undesirable resin swelling at reasonable temperatures (e.g. >95° C.).

One alternative for improving the desirability of the aforementioned types of anion exchange resins is to improve the activity of the catalyst by increasing the temperature at which the process is conducted. However, one potential drawback of the aforementioned conventional types of anionic exchange resins is their limited tolerance to high temperatures. Therefore, one publication discloses a catalyst system which employs a polymeric organosiloxane ammonium salt (see WO 97/19043) and another publication discloses a catalyst system which employs a bicarbonate form of an ion exchange resin that contains, as electropositive centers, nitrogen atoms linked to two or more atoms other than methyl group carbon atoms (see WO 97/33850). Both of these publications disclose their catalyst systems as being solutions to the potential problem with more conventional anion exchange resins which have been found under severe reaction conditions (high temperature and/or long service) to have unacceptable deterioration of alkylene glycol selectivity. One disadvantage of such catalyst systems is that they are typically more expensive as compared to the more conventional systems such as MSA-1 type catalyst.

It is desirable to have longer catalyst lifetimes and higher activity for the alkylene glycol preparation process, while utilizing the more conventional anion exchange resins.

SUMMARY OF THE INVENTION

In one aspect, the present invention is a process for preparing alkylene glycols which comprises reacting an alkylene oxide with water in the presence of an anion exchange resin and a combination of additives, wherein the combination of additives comprises carbon dioxide and an organic or inorganic base provided in an amount sufficient to maintain a pH of the reaction mixture between about 5.0 and 9.0, with the proviso that, when the base is bicarbonate or carbonate, then the anion exchange resin is a trimethyl benzyl ammonium anion exchange resin.

In a second aspect, the present invention is a process for preparing alkylene glycols which comprises reacting an alkylene oxide with water in the presence of an anion exchange resin and a combination of additives, wherein the combination of additives comprises carbon dioxide and an organic or inorganic base provided in an amount sufficient to maintain a resin swelling rate of less than 1.0% per day.

Surprisingly, the more conventional anion exchange resins can be utilized in the alkylene glycol preparation process by providing a combination of additives during the process. Contrary to prior teachings, it has been discovered that, for alkylene glycol synthesis, it is desirable for carbon dioxide to be present and that it is also necessary to maintain a pH of the reaction mixture between about 5.0 and 9.0. An advantage of this invention is that it provides desirable catalyst lifetime and activity, and provides a desirable selectivity to alkylene glycol, while at the same time minimizing resin swelling. Furthermore, this invention does not require that carbon dioxide, typically formed, during alkylene oxide production processes, be completely removed from the alkylene oxide before making the alkylene glycol.

DETAILED DESCRIPTION OF THE INVENTION

This invention is a process for preparing alkylene glycols from alkylene oxide and water. The preferred alkylene oxides include ethylene oxide, propylene oxide, and butylene oxide and the preferred alkylene glycols include their respective monoalkylene glycols: ethylene glycol (EG), propylene glycol (PG), and butylene glycol (BG). Most preferably, this invention is a process for preparing monoethylene glycol from ethylene oxide and water.

For the practice of this invention, all types of water may be used such as fresh water, deionized water, steam distilled water, and also distilled water produced from the dehydration process in the production of alkylene oxide and alkylene glycol. The water should be free of organic materials such as humic or fulvic acid that foul the anion exchange resin, but the water can contain glycols such as residual glycols from the separation of water and glycol product. The water should be free of metal ions, especially iron. The water is provided in an amount which is in a stoichiometric excess of that required for forming a desired glycol from reaction with epoxide. Preferably, the molar feed ratio of water to epoxide is at least about 1.1, more preferably at least about 2.0, and even more preferably at least about 5.0. Preferably, the molar feed ratio of water to epoxide is no more than about 30, more preferably no more than about 25, and even more preferably no more than about 20. Those of skill in the art will recognize that this ratio will vary depending upon the epoxide compounds employed, the reaction conditions, and the specific catalyst utilized.

In light of the disclosure herein, selection of a suitable anion exchange resin is within the skill in the art. Generally, such anion exchange resins include the aforementioned halogenate and/or bicarbonate-type anionic exchange resins, and carbonate and hydroxide-type exchange resins or a combination of any of the above, but do not include the metalate-type exchange resins with any possible electropositive centers. Illustrative of halogenate-type exchange resins is the disclosure of JP-A-57-139026 (incorporated herein by reference). Illustrative of bicarbonate-type exchange resins are the disclosures of WO 95/20559, WO 97/33850, RU Patent Nos. 2002726 and 2001901 (each of which is incorporated herein by reference). It is particularly preferred that the anion exchange resin contain quaternary ammonium groups. Examples of suitable, commercially available, anion exchange resins include: Amberlite™ IRA 400 and 900 series (based on polystyrene resins, cross-linked with divinylbenzene) (Rohm and Haas); Lewatit™ M 500 WS (Bayer); Duolite™ A 368, A-101D, ES-131 and A-161 (Rohm and Haas); and DOWEX™ MSA-1, MARATHON A, and MARATHON MSA (The Dow Chemical Company). Strong-base anion exchange resins with trimethyl benzyl ammonium groups (Type 1) are particularly preferred for this invention, as are resins based on polystyrene cross-linked with divinylbenzene.

The reaction of this invention is conducted in the presence of a combination of additives, comprising carbon dioxide and an organic or inorganic base. The carbon dioxide may be fed to the reaction in any convenient manner. The carbon dioxide may, for example, be introduced separately and/or with one or more of the feed streams. The carbon dioxide may be present in the alkylene oxide feed as a byproduct of the alkylene oxide production process. For example, EO typically has 0.0001–0.01 wt % $CO_2$. Thus no additional carbon dioxide is required if the amount present in the alkylene oxide feed is sufficiently high. The carbon dioxide may be present in the reaction mixture as dissolved carbon dioxide, in gaseous form, as carbonic acid, or in the form of salts of carbonic acid. Preferably, the carbon dioxide (or its equivalent, such as $NaHCO_3$) is present in the reaction mixture in a substantial amount, which is defined herein as an amount equal to or greater than 0.0001 wt %, more preferably 0.0005 wt %, most preferably 0.001 wt %. Preferably the carbon dioxide is present in the reaction mixture in an amount less than or equal to 0.1 wt %, preferably 0.05 wt %, more preferably 0.01 wt %. "Weight percent of carbon dioxide", as used herein, is based upon the total weight of carbon dioxide, or its equivalent, in the reaction mixture. "Reaction mixture" is meant to include each of the components fed to the reaction system, which includes at least the alkylene oxide, the water, and the combination of additives.

The other additive for the reaction of this invention is an organic or inorganic base. Such additive typically comprises any organic or inorganic bases such as alkylamines, pyridine, alkali phosphates, alkali sulphates, alkali carbonates, alkali bicarbonates, alkali metal hydroxide, and combinations thereof. "Bases", as used herein, shall be defined as compounds that, when added to water, give a pH of greater than 7.0. Preferably, the organic or inorganic base comprises sodium hydroxide (NaOH), sodium carbonate ($Na_2CO_3$), sodium bicarbonate ($NaHCO_3$), or any combination thereof. The organic or inorganic base is provided in an amount sufficient to maintain a pH of the reaction mixture at a lower limit of about 5.0, more preferably about 5.5, and most preferably about 6.0. For an upper pH limit, the organic or inorganic base is provided in an amount sufficient to maintain a pH of the reaction mixture less than or equal to about 9.0, preferably about 8.0, and more preferably about 7.0. By referring to "pH of the reaction mixture" it is meant the pH of the mixture which includes each of the components fed to the reaction system, including at least the alkylene oxide, the water, and the combination of additives. At high operating temperatures (e.g. >95° C.), it is preferable that the reaction pH be maintained at a lower level to avoid rapid degradation of the ion exchange resin.

The addition of $CO_2$ to water lowers the pH of the water. Pure water has a pH of 7.0. Water saturated with pure $CO_2$ at atmospheric pressure and 25° C. contains about 0.15 wt % $CO_2$ and has a pH of about 3.8. Water saturated with air (which contains 0.033 vol % $CO_2$) at atmospheric pressure and 25° C. contains about 0.00005 wt % $CO_2$ and has a pH of about 5.6. The addition of base to water that contains $CO_2$ increases the pH of the water without removing $CO_2$ from the water. The presence of alkylene oxide and/or alkylene glycols has little effect on pH.

The addition of alkali bicarbonate (e.g., $NaHCO_3$) to water increases the pH of the water from 7.0 to as high as 8.4, which is within the preferred range of pH. Therefore, if the carbon dioxide in the feed is present in the form of alkali bicarbonate, then no additional base is required. Furthermore, the addition of alkali bicarbonate is equivalent to adding equimolar amounts of $CO_2$ and alkali hydroxide; thus alkali bicarbonate can be considered a combination of additives for the purpose of this invention.

The addition of alkali carbonate (e.g., $Na_2CO_3$) to water increases the pH of the water from 7.0 to over 10.0, which is not within the preferred range of pH. Therefore, alkali carbonate is not preferred as the sole source of carbon dioxide additive, although it may be preferred as an inorganic base additive.

One embodiment of this invention is to conduct the process in an adiabatic reactor system such as a single reactor, or multiple reactors in series, with or without interstage cooling and staged feed addition. Another embodiment of this invention is to conduct the reaction in a reactive distillation process similar to as described in PCT International Patent Application Number PCT/US97/17936 (incorporated herein by reference).

The combination of additives of the present invention results in a relatively long catalyst lifetime. Longer catalyst lifetime is important in an industrial operation because it reduces the frequency of having to replace the catalyst.

A problem observed, especially in EO hydrolysis, has been one of resin swelling. In other words, the anion exchange resin grows over time, making it difficult to manage and control catalyst performance in an industrial process. Such resin swelling has been discovered to be a function of reaction temperature and EO concentration. The addition of the combination of additives as described herein minimizes the resin swelling problem as compared to no additives or only one additive.

Surprisingly, compared to other reactor types, using a combination of additives has been found to reduce the rate of continuous swelling of anion exchange resin catalyst which occurs under epoxide hydrolysis reaction conditions. It is known that ion exchange processes and solvents cause anion exchange resins to swell. This type of swelling is reversible, and the extent of swelling is limited. However, under conditions of alkylene oxide hydrolysis, especially EO hydrolysis, anion exchange resin catalyst unexpectedly swells continuously and irreversibly to an unlimited extent. Such continuous, unlimited swelling can create problems in an industrial situation, such as reactor plugging and a detrimental effect on selectivity.

Preferably, using the combination of additives of the present invention, the rate of continuous, unlimited swelling is reduced by at least 10% relative to the use of a single additive or no additives, more preferably at least about 20%, and even more preferably at least about 30%. Thus, for example, if the rate of continuous catalyst swelling is 1.5% per day using no additives, then the rate of continuous swelling using the combination of additives of the present invention is most preferably reduced to about 1.0% or less per day.

Of course, the rate of catalyst swelling will depend upon the specific catalyst. Moreover, more swelling can be tolerated with a catalyst having a higher activity. Preferably the rate of catalyst swelling is reduced to less than 1% per day, more preferably less than 0.9% per day, and even more preferably less than 0.8% per day.

Addition of the combination of additives also provides good alkylene oxide conversion and monoalkylene glycol selectivity. Percent conversion is defined as the amount of alkylene oxide that is reacted to form other products divided by the amount of alkylene oxide that is fed. Percent selectivity is calculated by dividing the number of moles of alkylene oxide consumed to form a given product divided by the total number of moles of alkylene oxide converted to all products. In the hydrolysis reactions of the present invention, selectivity for the monoalkylene glycol product is optimally higher than selectivity for the higher glycols.

In light of the disclosure herein, those of skill in the art are capable of optimizing the process conditions such as temperature, pressure, and water to alkylene oxide ratio, depending upon the reactor system utilized. Generally, though, the reaction temperature is typically in the range of from about 30° C. to about 150° C., preferably from about 50° C. to about 130° C. The reaction pressure is generally in the range of about 100 kPa to about 10000 kPa, preferably 500 kPa to about 5000 kPa.

The invention will be further clarified by a consideration of the following examples, which are intended to be purely exemplary of the use of the invention.

EXAMPLES

Preparation of the Catalyst

The catalyst used in the examples was DOWEX™ MSA-1, chloride anion form, with an exchange capacity of 1.3 milliequivalents per milliliter of wet resin. The chloride form of the resin was converted to the bicarbonate form for use in the examples.

Description of the Reactor

The reactor was a jacketed, 1.1 cm inner diameter, 23 cm long, 316 Stainless Steel tube. Heat transfer fluid at 95° C. was circulated through the jacket to maintain a constant, uniform reaction temperature. A 3.2 mm outer diameter thermocouple with six evenly spaced junctions was mounted concentrically inside the tube to measure the reaction temperature. The tube was packed with 20 ml of the resin catalyst. Aqueous and ethylene oxide feed streams were pumped at constant flow rates, mixed, and fed to the reactor. The reactor was operated at 12 bar to avoid vapor formation.

Example 1

Operation Without any Additives (Comparative Example)

Feed Solution

The ethylene oxide feed was 99.9% pure with an unknown amount of $CO_2$, and the feed rate was 8.3 g/h. The aqueous feed was 64 g/h of deionized, $CO_2$-free water (18 MΩ resistance, pH 7.0).

Results

The products were analyzed by gas chromatography for ethylene oxide (EO), mono-ethylene glycol (MEG), diethylene glycol (DEG), and triethylene glycol (TEG). At the beginning of the experiment, the average reactor temperature was 97.8° C., EO conversion was 95.7%, EG selectivity was 98.8%, DEG selectivity was 1.2%, and TEG selectivity was less than 0.01%. Molar selectivity is calculated by dividing the number of moles of EO consumed to form a given product divided by the total number of moles of EO converted to all products. The run was continued for 180 days to measure conversion, selectivity, catalyst deactivation, and resin expansion. After 42 days, the resin had expanded to 35 ml; 15 ml were removed and 20 ml were reloaded into the reactor. After 143 days, the reloaded resin had expanded to 40 ml; 20 ml were removed and 20 ml were reloaded into the reactor. After 153 days, the water and EO feed rates were reduced by 50% to compensate for catalyst removal and deactivation. At the end of the run (180 days), the average reactor temperature was 95.2° C., EO conversion was 66.4%, EG selectivity was 95.1%, DEG selectivity was 4.6%, and TEG selectivity was 0.3%. The catalyst half-life (i.e., time required for the catalyst to lose 50% of its activity) was determined to be 357±7 days. The removal of catalyst, change in average reactor temperature, and reduction of feed rates were accounted for in determining the catalyst half-life. The resin expanded at a rate of 1.5±0.1%/day.

Example 2

Operation With $CO_2$ Only, But No Organic or Inorganic Base (Comparative Example)

Feed Solution

The ethylene oxide feed was 99.9% pure with an unknown amount of $CO_2$, and the feed rate was 8.2 g/h. The aqueous feed was 64 g/h water saturated with 10% $CO_2$ in helium at 23° C. and 1 atm (pH 4.4). The combined aqueous and EO feed had 0.014 wt % $CO_2$.

Results

At the beginning of the experiment, the average reactor temperature was 96.6° C., EO conversion was 80.1%, EG selectivity was 98.4%, DEG selectivity was 1.6%, and TEG selectivity 0.03%. The experiment was not continued at the same conditions because the catalyst activity was too low to be of commercial interest; therefore, catalyst half-life and swelling rate were not measured at the conditions used in this example.

Example 3

Operation With NaOH Only, But No $CO_2$ (Comparative Example)

Feed Solution

The ethylene oxide feed was 99.9% pure with an unknown amount of $CO_2$, and the feed rate was 8.2 g/h. The aqueous feed was 64 g/h water with 0.011 wt % NaOH (pH 11.2). The combined aqueous and EO feed had 0.01 wt % NaOH.

Results

After two days of feeding the NaOH solution, the average reactor temperature was 98.4° C., EO conversion was at a maximum of 99.7%, EG selectivity was 92.1%, DEG selectivity was 7.6%, and TEG selectivity 0.35%. After two more days, the reactor temperature was unchanged, EO conversion was 99.2%, EG selectivity was 91.8%, DEG selectivity was 7.8%, and TEG selectivity 0.42%. The run was stopped at that point because the catalyst had expanded and completely filled the reactor, thereby preventing flow through the catalyst bed. The final catalyst volume was 28 ml; the expansion rate was 7.7%/day. The catalyst half-life was 6.9±0.4 days.

Example 4

Operation With $Na_2CO_3$ Only (Comparative Example)

Feed Solution

The ethylene oxide feed was 99.9% pure with an unknown amount of $CO_2$, and the feed rate was 8.2 g/h. The aqueous feed was 64 g/h water with 0.03 wt % $Na_2CO_3$ (pH 10.5). The combined aqueous and EO feed had 0.027 wt % $Na_2CO_3$.

Results

After two days of feeding the $Na_2CO_3$ solution, the average reactor temperature was 98.3° C., EO conversion was at a maximum of 99.8%, EG selectivity was 96.7%, DEG selectivity was 3.2%, and TEG selectivity 0.06%. After eight more days, the average reactor temperature was 98.7° C., EO conversion was 98.4%, EG selectivity was 96.6%, DEG selectivity was 3.3%, and TEG selectivity 0.07%. The run was stopped at that point because the catalyst had expanded and completely filled the reactor, thereby preventing flow through the catalyst bed. The final catalyst volume was 28 ml; the expansion rate was 3.9%/day. The catalyst half-life was 12.5±0.3 days.

Example 5

Operation With a Combination of Additives, $CO_2$ and NaOH

Feed Solution

The ethylene oxide feed was 99.9% pure with an unknown amount of $CO_2$, and the feed rate was 8.2 g/h. The aqueous feed was 32 g/h water saturated with 20% $CO_2$ in $N_2$ at 23° C. and 1 atm, and 32 g/h water with 0.023 wt % NaOH. The combined aqueous feed had a pH of 7.0, and the total combined feed had 0.014 wt % $CO_2$ and 0.01 wt % NaOH.

Results

After eight days of stable operation, the average reactor temperature was 99.0° C., 10 EO conversion was 93.0%, EG selectivity was 98.8%, DEG selectivity was 1.2%, and TEG selectivity 0.01%. The run was continued for 180 days to measure conversion, selectivity, catalyst deactivation, and resin expansion. After 95 days, the resin had expanded to 31 ml; 11 ml were removed and 20 ml were reloaded into the reactor. After 157 days, the water and EO feed rates were reduced by 25% to compensate for catalyst removal and deactivation. At the end of the run (180 days), the average reactor temperature was 96.9° C., EO conversion was 71.9%, EG selectivity was 98.5%, DEG selectivity was 1.5%, and TEG selectivity was 0.04%. The catalyst half-life was determined to be 394±7 days. The removal of catalyst and reduction of feed rates were accounted for in determining the catalyst half-life. The resin expanded at a rate of 0.7±0.04%/day.

Example 6

Operation With $NaHCO_3$, Equivalent to Equimolar Addition of $CO_2$ and NaOH

Feed Solution

The ethylene oxide feed was 99.9% pure with an unknown amount of $CO_2$, and the feed rate was 8.2 g/h. The aqueous feed was 64 g/h water with 0.024 wt % $NaHCO_3$ (pH 8.1; equivalent to a solution with 0.013 wt % $CO_2$ and 0.011 wt % NaOH). The combined aqueous and EO feed had 0.021 wt % $NaHCO_3$ (equivalent to a solution with 0.011 wt % $CO_2$ and 0.01 wt % NaOH).

Results

After two days of feeding the $NaHCO_3$ solution, the average reactor temperature was 98.5° C., EO conversion was at a maximum of 97.2%, EG selectivity was 98.8%, DEG selectivity was 1.2%, and TEG selectivity 0.02%. After four more days, the reactor temperature was unchanged, EO conversion and glycol selectivities were unchanged. The run was stopped at that point because the catalyst bed overheated due to loss of water supply. The final catalyst volume was 21.5 ml; the expansion rate was 1.1%/day. There was no catalyst deactivation during the run, so the half-life could not be determined.

The following table is a summary of the examples. The selectivities at 180 days can be directly compared because the EO conversion was about the same in each example.

TABLE 1

Comparison of Examples 1–6

| Example: | 1[a] | 2[a] | 3[a] | 4[a] | 5 | 6 |
|---|---|---|---|---|---|---|
| Additional $CO_2$ in feed (wt %) | 0 | 0.014 | 0 | 0 | 0.014 | 0.011[d] |
| Base added | none | none | NaOH | $Na_2CO_3$ | NaOH | $NaHCO_3$ |
| Base in feed (wt %) | 0 | 0 | 0.010 | 0.027 | 0.010 | 0.021 |
| Feed pH | 7.0 | 4.4 | 11.2 | 10.5 | 7.0 | 8.1 |
| Initial Temperature (° C.) | 97.8 | 96.6 | 98.4 | 98.3 | 99.0 | 98.5 |
| Final Temperature (° C.)[b] | 95.2 | | | | 96.9 | |
| Initial EO conversion (%) | 95.7 | 80.1 | 99.7 | 99.8 | 93.0 | 97.2 |
| Final EO conversion (%)[b] | 66.4 | | | | 71.9 | |
| Initial EG selectivity (%) | 98.8 | 98.4 | 92.1 | 96.7 | 98.8 | 98.8 |
| Final EG selectivity (%)[b] | 95.1 | | | | 98.5 | |
| Initial DEG selectivity (%) | 1.2 | 1.6 | 7.6 | 3.2 | 1.2 | 1.2 |
| Final DEG selectivity (%)[b] | 4.6 | | | | 1.5 | |
| Initial TEG selectivity (%) | <0.01 | 0.03 | 0.35 | 0.06 | 0.01 | 0.02 |
| Final TEG selectivity (%)[b] | 0.3 | | | | 0.04 | |
| Catalyst half-life (days) | 357 ± 7 | n.d.[c] | 6.9 ± 0.4 | 12.5 ± 0.3 | 394 ± 7 | n.d.[c] |
| Swelling rate (%/day) | 1.5 ± 0.1 | n.d.[c] | 7.7 | 3.9 | 0.7 ± 0.04 | 1.1 |

[a]Comparative example.
[b]Final values are at 180 days.
[c] Not determined.
[d]Added as $NaHCO_3$.

Compared to the system with no feed additives (Example 1), the $CO_2$-only additive system (Example 2) has much lower catalyst activity and lower EG selectivity, and the base-only additive systems (Examples 3 and 4) has much lower EG selectivity and catalyst lifetime and a much higher swelling rate. Therefore, neither the $CO_2$-only additive system nor the base-only additive systems offer advantages over a system with no additives. However, the combination of $CO_2$ and base additives or its equivalent as bicarbonate (Examples 5 and 6) provides several unexpected benefits versus a system without these additives or with only one of these additives. Compared to the system with no additives, the combined $CO_2$/base additive system maintains the high EG selectivity for several months, increases the catalyst lifetime, and reduces the catalyst swelling rate without significantly reducing catalyst activity. The combined $CO_2$/base additive system gives much higher catalyst activity and higher EG selectivity than the $CO_2$-only system. The combined $CO_2$/base additive system gives much higher EG selectivity and catalyst life and much lower catalyst swelling than the base-only system.

Other embodiments of the invention will be apparent to those skilled in the art from a consideration of this specification or practice of the invention disclosed herein. It is intended that the specification and example be considered as exemplary only, with the true scope and spirit of the invention being indicated by the following claims.

What is claimed is:

1. A process for preparing alkylene glycols directly from an alkylene oxide and water, which comprises reacting the alkylene oxide with water in the presence of an anion exchange resin and a combination of additives, wherein the combination of additives comprises carbon dioxide and an organic or inorganic base provided in an amount sufficient to maintain a pH of the reaction mixture between about 5.0 and 9.0, with the proviso that, when the base is bicarbonate or carbonate, then the anion exchange resin is a trimethyl benzyl ammonium anion exchange resin.

2. The process of claim 1 wherein the carbon dioxide is present as dissolved carbon dioxide, gaseous carbon dioxide, as carbonic acid, or as a salt of carbonic acid.

3. The process of claim 1 wherein the anions of the anion exchange resin consist essentially of halogen anions, bicarbonate anions, carbonate anions, hydroxide anions, or a combination thereof.

4. The process of claim 1 wherein the anion exchange resin is based on polystyrene cross-linked with divinylbenzene.

5. The process of claim 1 wherein the anion exchange resin is of the quaternary ammonium type with trimethyl benzyl ammonium groups.

6. The process of claim 1 wherein the organic or inorganic base comprises a compound selected from alkylamines, pyridine, alkali phosphates, alkali sulphates, alkali carbonates, alkali bicarbonates, alkali metal hydroxide, and combinations thereof.

7. The process of claim 6 wherein the organic or inorganic base is sodium hydroxide sodium carbonate, sodium bicarbonate, or any combination thereof.

8. The process of claim 1 wherein the alkylene oxide is ethylene oxide or propylene oxide and the alkylene glycol is monoethylene glycol or monopropylene glycol.

9. The process of claim 1 wherein the carbon dioxide is provided to the reaction in an amount between about 0.0001 weight percent and about 0.1 weight percent of the reaction mixture.

10. The process of claim 1 wherein the process is conducted in an adiabatic reactor system, an isothermal reactor system, or a combination thereof.

11. The process of claim 1 wherein the molar feed ratio between of water to alkylene oxide is in the range of from about 1.1:1 to about 30:1.

12. A process for preparing alkylene glycols directly from and alkylene oxide and water, which comprises reacting the alkylene oxide with water in the presence of an anion exchange resin and a combination of additives, wherein the combination of additives comprises carbon dioxide and an organic or inorganic base provided in an amount sufficient to maintain a resin swelling rate of less than 1.0% per day.

13. The process of claim 12 wherein the combination of additives is provided in an amount sufficient to maintain a pH of the reaction mixture between about 5.0 and 9.0.

14. The process of claim 12 wherein the anions of the anion exchange resin consist essentially of halogen anions, bicarbonate anions, carbonate anions, hydroxide anions, or a combination thereof.

15. The process of claim 12 wherein the anion exchange resin is of the quaternary ammonium type.

16. The process of claim 12 wherein the organic or inorganic base comprises a compound selected from alkylamines, pyridine, alkali phosphates, alkali sulphates, alkali carbonates, alkali bicarbonates, alkali metal hydroxide, and combinations thereof.

17. The process of claim 16 wherein the organic or inorganic base is sodium hydroxide sodium carbonate, sodium bicarbonate, or any combination thereof.

18. The process of claim 12 wherein the carbon dioxide is provided to the reaction in an amount between about 0.0001 weight percent and about 0.1 weight percent of the reaction mixture.

19. The process of claim 12 wherein the process is conducted in an adiabatic reactor system, an isothermal reactor system, or a combination thereof.

20. The process of claim 12 wherein the molar feed ratio of water to alkylene oxide is from about 1.1:1 to about 30:1.

* * * * *